(12) United States Patent
Okoba et al.

(10) Patent No.: US 10,391,424 B2
(45) Date of Patent: Aug. 27, 2019

(54) FRACTION COLLECTOR

(71) Applicant: SHIMADZU CORPORATION, Kyoto (JP)

(72) Inventors: Tsutomu Okoba, Kyoto (JP); Takayuki Iriki, Fulton, MD (US)

(73) Assignee: SHIMADZU CORPORATION, Kyoto-shi (JP)

( * ) Notice: Subject to any disclaimer, the term of this patent is extended or adjusted under 35 U.S.C. 154(b) by 259 days.

(21) Appl. No.: 15/072,618

(22) Filed: Mar. 17, 2016

(65) Prior Publication Data

US 2016/0288016 A1 Oct. 6, 2016

(30) Foreign Application Priority Data

Apr. 3, 2015 (JP) ................. 2015-076408

(51) Int. Cl.
- *B01D 15/24* (2006.01)
- *G01N 30/80* (2006.01)
- *G01N 30/82* (2006.01)
- *B01D 15/10* (2006.01)

(52) U.S. Cl.
CPC ........... *B01D 15/247* (2013.01); *B01D 15/24* (2013.01); *G01N 30/80* (2013.01); *G01N 30/82* (2013.01); *B01D 15/10* (2013.01)

(58) Field of Classification Search
CPC ...... B01D 15/22; B01D 15/24; B01D 15/247; B01D 15/10; G01N 30/82; G01N 30/88; G01N 30/8665; G01N 30/80
See application file for complete search history.

(56) References Cited

U.S. PATENT DOCUMENTS

| | | | |
|---|---|---|---|
| 4,166,483 | A | 9/1979 | Nordlund |
| 2004/0238427 | A1 | 12/2004 | Maruyama et al. |
| 2006/0054544 | A1 | 3/2006 | Roenneburg et al. |
| 2011/0184658 | A1 | 7/2011 | Maruyama |

(Continued)

FOREIGN PATENT DOCUMENTS

| | | |
|---|---|---|
| CN | 1573329 A | 2/2005 |
| CN | 2938091 Y | 8/2007 |
| CN | 101014396 A | 8/2007 |

(Continued)

OTHER PUBLICATIONS

Office Action dated May 10, 2017, issued in counterpart Chinese Patent Application No. 201511000865.9, with English translation. (21 pages).

(Continued)

*Primary Examiner* — Benjamin L Lebron
(74) *Attorney, Agent, or Firm* — Westerman, Hattori, Daniels & Adrian, LLP

(57) ABSTRACT

A moving section that moves in the horizontal plane direction at above a collection container section where collection containers are set is provided with a nozzle holding section for holding a nozzle, and a waste port holding section for holding a waste port. The moving section is capable of moving the nozzle holding section or the waste port holding section. Accordingly, one of a state where the waste port is at a position immediately below the tip of the nozzle and a state where the waste port is not at the position immediately below the tip of the nozzle may be achieved.

3 Claims, 3 Drawing Sheets

(56) References Cited

U.S. PATENT DOCUMENTS

2013/0316336 A1* 11/2013 Matsui .............. G01N 35/1095
　　　　　　　　　　　　　　　　　　　　　435/6.1

FOREIGN PATENT DOCUMENTS

| CN | 102124329 A | 7/2011 |
| JP | H04329356 A | 11/1992 |
| JP | 07-140127 A | 6/1995 |
| JP | 09-274025 A | 10/1997 |
| JP | 2005-331436 A | 12/2005 |
| JP | 2010-014559 A | 1/2010 |
| JP | 2010-14559 A | 1/2010 |
| JP | 2012-173059 A | 9/2012 |
| SU | 1357840 A1 | 12/1987 |
| WO | 2010/021008 A1 | 2/2010 |

OTHER PUBLICATIONS

Office Action dated May 29, 2018, issued in counterpart Japanese application No. 2015-076408, with English translation. (6 pages).

\* cited by examiner

FRACTION COLLECTOR

BACKGROUND OF THE INVENTION

1. Field of the Invention

The present invention relates to a fraction collector for fractionating and collecting a sample component separated by a liquid chromatograph.

2. Description of the Related Art

A fraction collector of a high performance liquid chromatograph includes a nozzle from which a sample component flowing out from an outlet of a detector of the high performance liquid chromatograph is to drop. A three-way electromagnetic valve is provided between the outlet of the detector and the nozzle, and the three-way electromagnetic valve switches between whether an outflow liquid from the detector is to drop from the nozzle or is to be discarded to a drain. The nozzle is moved, in a horizontal plane direction, above a rack where a collection container for collecting a sample component is set, and is placed above an empty collection container. An outflow liquid from the detector is discarded to the drain until a sample component is detected by the detector, but when a sample component is detected by the detector, the three-way electromagnetic valve is switched to cause the sample component to drop from the nozzle, and the sample component is collected in the collection container.

SUMMARY OF THE INVENTION

Generally, a fraction collector has a function of automatically determining a peak of a component desired by an analyst to be collected, by capturing a signal in a chromatogram from a detector such as an ultraviolet absorbance detector or a mass spectrometer of a liquid chromatograph, and by processing the waveform of the signal by software or firmware (see JP 2010-14559 A). When the power of the fraction collector is turned on, the nozzle moves in the horizontal plane to the position above an empty collection container. A portion which is determined as a result of waveform processing on the chromatograph signal from the detector to be not a peak is discarded to the drain, and the peak portion is caused to drop into the empty collection container from the nozzle.

When the three-way electromagnetic valve is switched after a target sample component has been collected in the collection container, the sample component possibly remains between the valve of the electromagnetic valve and the tip portion of the nozzle. When there is a remaining sample component, a problem may arise that a previously remaining component gets mixed in at the time of collection of the next sample component in another collection container.

To solve the problem described above, it is proposed and also performed to move the nozzle to above another collection container or above a drain port provided at a predetermined position after collection of a sample component is completed, and to switch the three-way electromagnetic valve again to cause the liquid to drop from the nozzle tip to thereby perform purging from the electromagnetic valve to the nozzle tip. However, if purging is performed above another collection container, this results in the problem of wasteful consumption of collection containers. Further, if purging is performed by moving the nozzle to above a drain port, the distance of movement of the nozzle for purging is increased, and there is a problem that a sample component to be collected reaches the nozzle while the nozzle is being moved, and that a valuable sample component is partially not collected due to the nozzle not being placed above a predetermined collection container in time.

A fraction collector according to the present invention includes a collection container section, a moving section, a nozzle, a nozzle holding section, a waste port, a waste port holding section, and a drive mechanism. The collection container section is a region, provided inside the device, for setting a collection container. The top of a collection container set in the collection container section is open so as to collect a sample flowing out of a detector of a liquid chromatograph. The moving section moves in a horizontal plane direction at above the collection container section. The nozzle is connected to a channel through which a liquid flowing out of the detector flows. The nozzle holding section is provided at the moving section. The nozzle holding section holds the nozzle in such a way that a tip of the nozzle faces downward. The waste port has its top open, and is for leading a waste liquid to a drain. The waste port holding section is provided at the moving section, and holds the waste port. The drive mechanism moves the nozzle holding section or the waste port holding section so as to selectively achieve a state where the waste port is at a position immediately below the tip of the nozzle or a state where the waste port is not at the position immediately below the tip of the nozzle.

According to such a structure, after dropping of a sample component from the tip of the nozzle into a collection container is completed, the waste port may be placed at the position immediately below the tip of the nozzle, and a liquid not containing the sample component may be made to drop from the tip of the nozzle to the waste port. Accordingly, after the sample component has dropped into the collection container, the inside of a channel up to the tip of the nozzle may be purged without having the nozzle moved. It is therefore not necessary to cause a liquid to drop from the tip of the nozzle into another collection container, or to move the nozzle to the waste port provided at a position different from the collection container section and perform purging.

DETAILED DESCRIPTION OF THE INVENTION

As a further preferred embodiment of a fraction collector according to the present invention, a collection operation section and a purge operation section are further included. The collection operation section performs a collection operation of achieving, when a peak originating from a sample component is detected based on a detection signal of a detector, a state where a waste port is not present at a position immediately below a nozzle, before the liquid at the part corresponding to the peak reaches the nozzle tip, and of causing the liquid at the part corresponding to the peak to drop from the nozzle tip into a collection container for collecting the component corresponding to the peak. The purge operation section performs a purge operation of achieving, based on a detection signal of the detector, a state where the waste port is present at a position immediately below the nozzle, after the collection operation is completed, and of causing a liquid not containing a sample component to drop from the nozzle tip.

The purge operation section is desirably configured to perform the purge operation in a state where a moving section is placed at a position at which the next sample component will be dropped into a collection container for collecting the sample component. Then, even if the peak of the next sample component is detected during a purge operation or immediately after completion of a purge operation, the collection operation for the component may be immediately started, and a failure to collect a part of the sample component may be prevented.

As a waste port holding section, an arm extending in a horizontal direction for holding the waste port at a position lower than the nozzle tip may be cited. In this case, a drive mechanism may move, by rotating the arm, the waste port to a position immediately below the nozzle tip and to a position different from the position immediately below the nozzle tip. This allows the structure of the drive mechanism to be simple.

Figure 1:
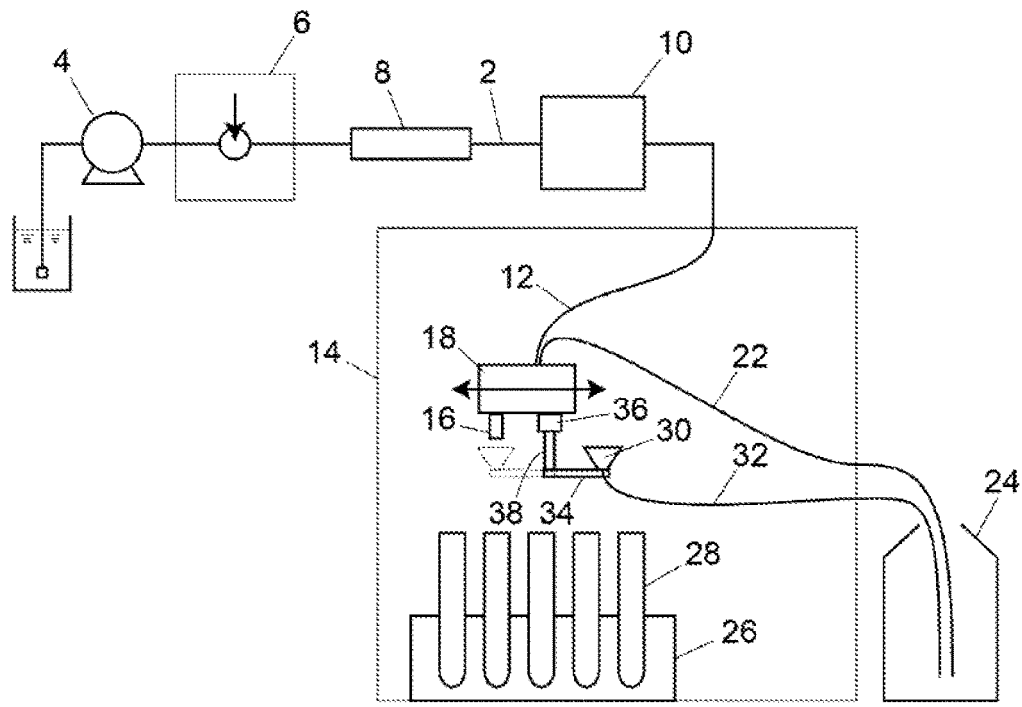
FIG. 1 is a schematic configuration diagram showing an example of a fraction collector together with a liquid chromatograph.

An example of a preparative liquid chromatograph provided with the fraction collector will be described with reference to FIGS. 1 and 2.

A fraction collector 14 is connected at a downstream end of an analysis channel 2 of the liquid chromatograph. The analysis channel 2 is a channel through which a mobile phase that is delivered by a delivery pump 4 flows. An autosampler 6, an analytical column 8, and a detector 10 are provided on the analysis channel 2, from the upstream side. An analysis sample is injected into the analysis channel 2 by the autosampler 6, and is separated into components by the analytical column 8. The separated sample components are detected by the detector 10, and are then fractionated and collected on a per sample component basis at the fraction collector 14.

The fraction collector 14 includes a nozzle 16 for causing a sample component flowing out of an outlet of the detector 10 to drop. The nozzle 16 is held by a nozzle head 18 (moving section). A rack 26 (collection container section) is provided inside the fraction collector 14. The nozzle head 18 moves in the horizontal plane direction above collection containers 28 set in the rack 26.

Figure 2:
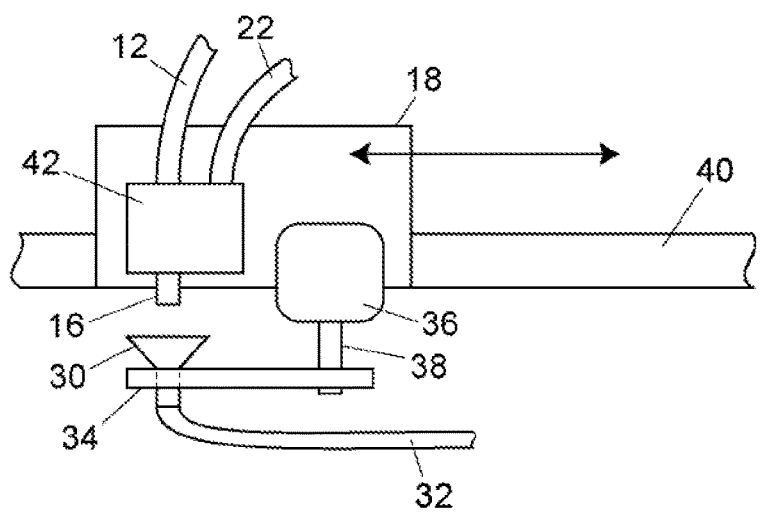
FIG. 2 is a diagram schematically showing a nozzle head portion of the present example.

As shown in FIG. 2, the nozzle head 18 is mounted on an X-axis rail 40 provided extending in an X-axis direction (a left/right direction in the drawing), which is one direction on the horizontal plane. The nozzle head 18 moves in the X-axis direction along the X-axis rail 40 by driving of an X-axis motor 46 (see FIG. 3) not shown in FIG. 2. The X-axis rail 40 is supported by a Y-axis rail (not shown) provided extending in a Y-axis direction (a direction perpendicular to the page of the drawing) that is orthogonal to the X-axis direction on the horizontal plane. The X-axis rail 40 moves in the Y-axis direction along the Y-axis rail by driving of a Y-axis motor 48 (see FIG. 3) not shown in FIG. 2. The nozzle 16 held by the nozzle head 18 moves in the horizontal plane direction at above the rack 26 by driving of the X-axis motor 46 and the Y-axis motor 48.

An electromagnetic valve 42 is provided to the nozzle head 18. The nozzle 16 is provided extending downward from the electromagnetic valve 42. The tip of the nozzle 16 faces vertically downward. The electromagnetic valve 42 is a three-way electromagnetic valve provided with one common port and two selection ports. The nozzle 16 is connected to one of the selection ports of the electromagnetic valve 42. A drain channel 22 leading to a waste liquid container 24 is connected to the other of the selection ports of the electromagnetic valve 42. A channel 12 leading to the outlet of the detector 10 is connected to the common port of the electromagnetic valve 42. The electromagnetic valve 42 switches to one of a state where the channel 12 from the detector 10 is connected to the nozzle 16 (hereinafter "nozzle 16 side") and a state where the channel 12 is connected to the drain channel 22 (hereinafter "drain side").

A waste port 30 is provided to the nozzle head 18. The waste port 30 is connected to the waste liquid container 24 by a channel 32. The waste port 30 is held at a tip end side of an arm 34 extending in the horizontal direction, with an opening section facing upward. A base end section of the arm 34 is supported by a drive shaft 38 of a waste port drive motor 36. The arm 34 is rotated in the horizontal plane by the waste port drive motor 36. The waste port 30 is placed, by rotation of the arm 34, at a position directly below the nozzle 16 or at a position that is offset from directly below the nozzle 16. FIG. 1 shows a state where the arm 34 has placed the waste port 30 at the position immediately below the nozzle 16, and a state where it has rotated 180 degrees therefrom, but any rotation angle is allowed for the arm 34 as long as the waste port 30 may be placed at a position that is offset from the position immediately below the nozzle 16.

Figure 3:
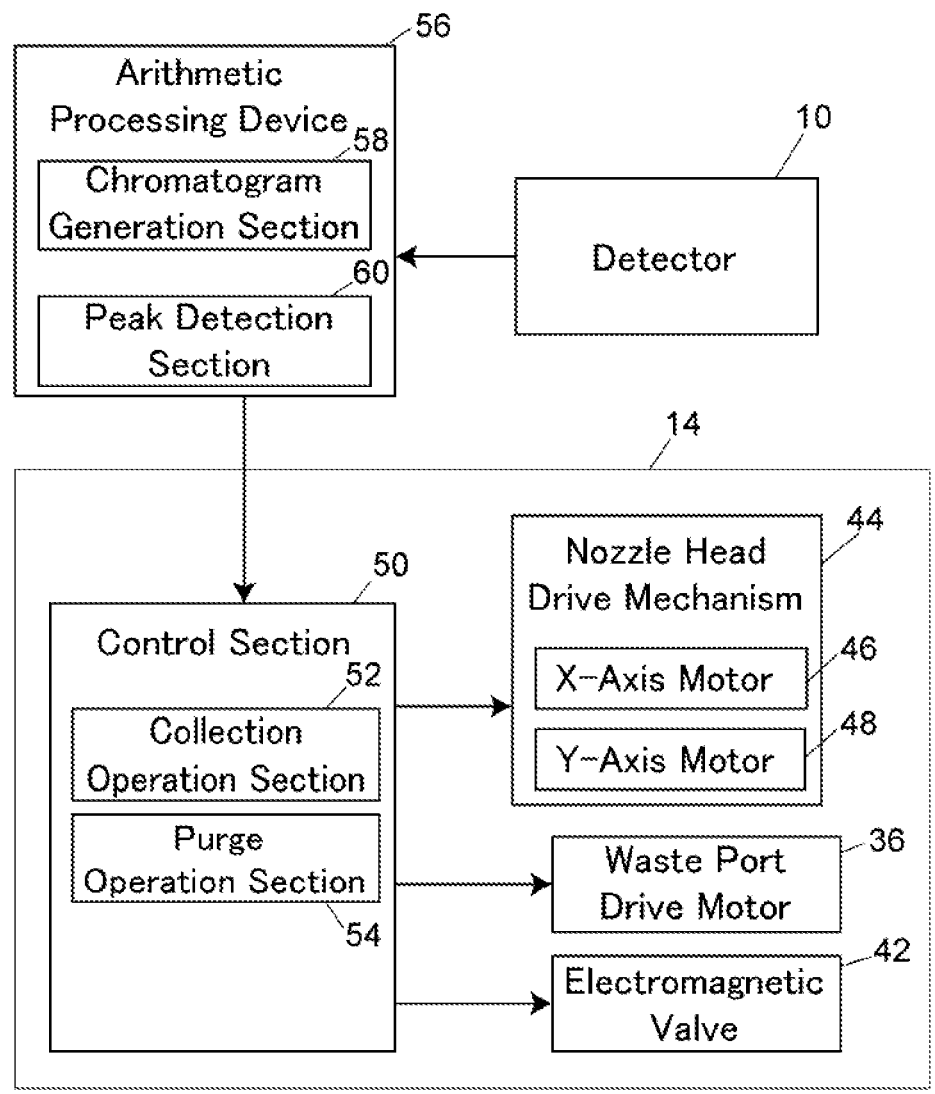
FIG. 3 is a block diagram showing a control system of the present example.

Next, a control system of the present example will be described with reference to FIG. 3.

The fraction collector 14 includes a control section 50. The control section 50 controls operations of the waste port drive motor 36, a nozzle head drive mechanism 44, and the electromagnetic valve 42. The nozzle head drive mechanism 44 is configured from the X-axis motor 46 for driving the nozzle head 18 in the X-axis direction, and the Y-axis motor 48 for driving the nozzle head 18 in the Y-axis direction. The control section 50 is electrically connected to an arithmetic control device 56 that is provided separately from the fraction collector 14. The control section 50 captures a signal from the arithmetic control device 56, and performs control based on the signal. The control section 50 is configured from a computer and a storage device provided inside the fraction collector 14. Various types of information are stored in the storage device. The arithmetic control device 56 is realized by, for example, a general-purpose personal computer, or a dedicated computer such as a system controller.

The arithmetic control device 56 includes a chromatogram generation section 58, and a peak detection section 60. The chromatogram generation section 58 captures detection signals from the detector 10, and successively generates chromatograms at regular intervals based on the detection signals. The peak detection section 60 detects a start point and an end point of a peak originating from a sample component, based on the chromatogram that is generated by the chromatogram generation section 58. When a start point and an end point of a peak originating from a sample component are detected by the peak detection section 60, a signal regarding the same is captured by the control section 50.

The control section 50 includes a collection operation section 52, and a purge operation section 54. The collection operation section 52 and the purge operation section 54 are functions that may be realized by the computer configuring the control section 50 executing programs stored in the storage device.

The collection operation section 52 is configured to control the operations of the electromagnetic valve 42 and the nozzle head drive mechanism 44 so that, of the liquid flowing out of the detector 10, only the liquid containing a sample component drops from the nozzle 16 into a predetermined collection container 28. That is, the collection operation section 52 has the channel 12 connected to the channel 22 side by the electromagnetic valve 42 until a peak start point is detected in a chromatogram, which is generated based on a detection signal of the detector 10, and discards the liquid not containing the sample component to the waste liquid container 24. When a peak start point is detected in the generated chromatogram, the electromagnetic valve 42 is switched to place the nozzle 16 above a predetermined collection container 28 and to connect the channel 12 to the nozzle 16 side so as to cause the liquid at the part corresponding to the peak to drop into the predetermined collection container 28 until the end point of the peak is detected. During this collection operation, the waste port 30 is in standby at a position different from the position immediately below the nozzle 16.

The purge operation section 54 is configured to place the waste port 30 at the position immediately below the nozzle 16 after the collection operation described above is completed, and to cause a mobile phase not containing a sample component, flowing out of the detector 10, to drop from the tip of the nozzle 16 to the waste port 30. The internal channel up to the tip of the nozzle 16 is thereby washed. This purge operation is desirably performed in a state where the nozzle 16 is placed above a collection container for collecting the next sample component. Then, when the next peak is detected during the purge operation, the collection operation for the sample component corresponding to the peak may be swiftly performed simply by moving the waste port 30, without moving the nozzle head 18, and the failure to collect a part of the sample component may be prevented.

Figure 4:
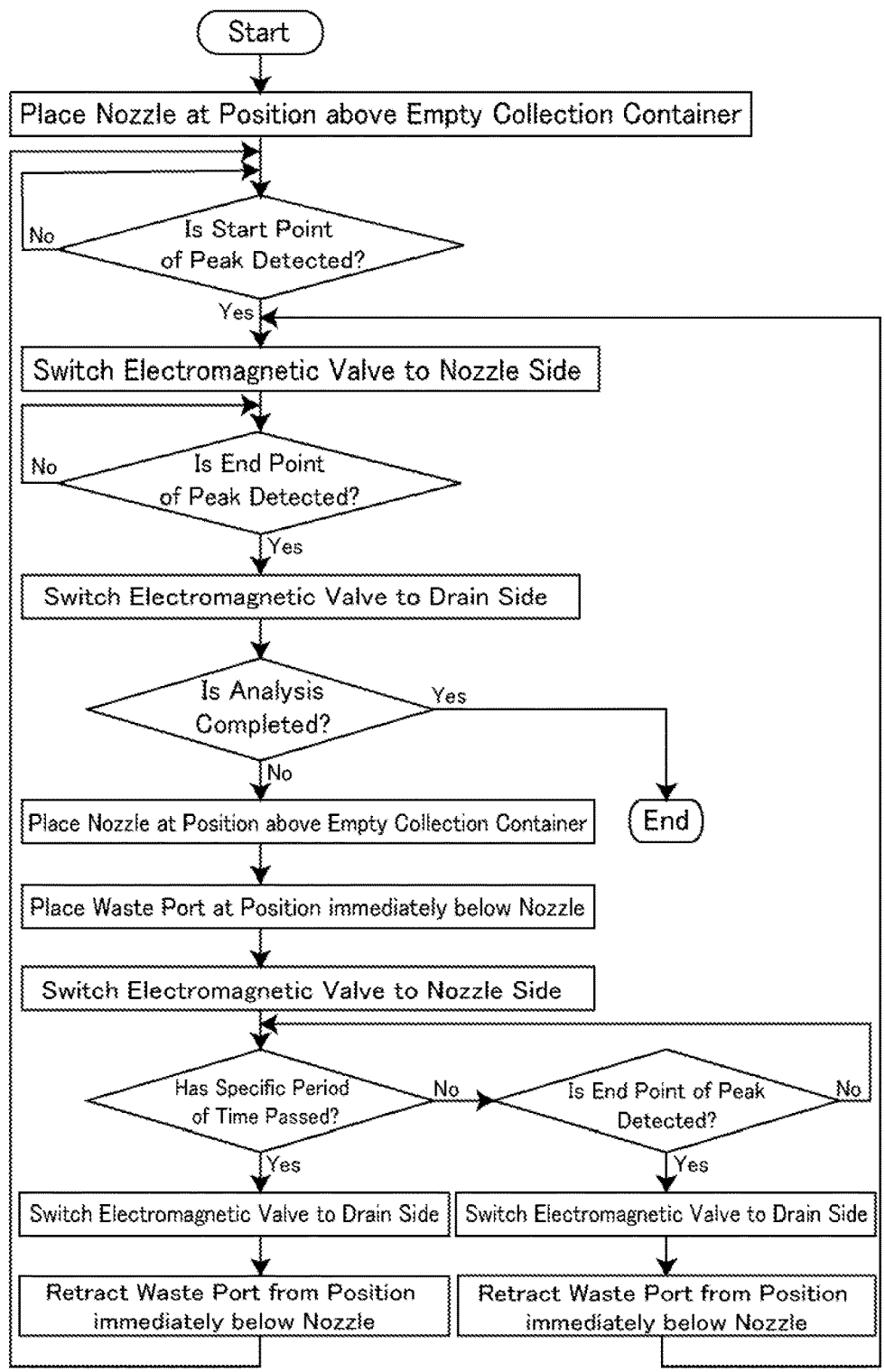
FIG. 4 is a flow chart showing a series of component collection operations according to the present example.

An operation of the fraction collector 14 of the present example will be described with reference to FIG. 4.

The electromagnetic valve 42 is switched to the drain side before delivery of a mobile phase by the delivery device 4 is started. The waste port 30 is placed in standby in a state of being offset from the position immediately below the nozzle 16. When analysis is started, the nozzle head 18 is moved, and the nozzle 16 is placed above an empty collection container 28 and is placed in standby until a peak start point is detected in the chromatogram generated based on a detection signal of the detector 10. When a peak start point is detected, the electromagnetic valve 42 is switched to the nozzle 16 side at the timing of the liquid at the part corresponding to the peak reaching the electromagnetic valve 42, and the liquid drops from the tip of the nozzle 16 and is collected in the empty collection container 28. When a peak end point is detected, the electromagnetic valve 42 is switched to the drain side at a timing after the liquid at the end point part has passed through the electromagnetic valve 42.

When analysis of the sample is to be continued, the nozzle head 18 is moved, and the nozzle 16 is placed at a position above the next empty collection container 28. The waste port 30 is placed at the position immediately below the nozzle 16, and the electromagnetic valve 42 is switched to the nozzle 16 side. A mobile phase not containing a sample component thereby drops into the waste port 30 from the tip of the nozzle 16, and the internal channel up to the tip of the nozzle 16 is washed. This purge operation is performed for a specific period of time, and when the specific period of time has passed, the electromagnetic valve 42 is switched to the drain side, the waste port 30 is retracted from the position immediately below the nozzle 16, and standby is performed until the next peak is detected.

In the case where the start point of the next peak is detected before the purge operation is completed, the electromagnetic valve 42 is switched to the drain side and the waste port 30 is kept retracted from the position immediately below the nozzle 16 until the liquid at the part corresponding to the peak reaches the electromagnetic valve 42. Then, the electromagnetic valve 42 is switched to the nozzle 16 side at the time of the liquid at the part corresponding to the peak reaching the electromagnetic valve 42, and collection of the sample component is performed.

In the example described above, the arm 34 and the waste port drive motor 36 for rotating the arm 34 configure the drive mechanism for switching between a state where the waste port 30 is at the position immediately below the nozzle 16 and a state where it is not. However, the drive mechanism according to the present invention is not limited to the one described above. For example, switching between the state where the waste port 30 is at the position immediately below the nozzle 16 and the state where it is not may be performed by moving the nozzle 16 independently of the nozzle head 18.

What is claimed is:

1. A fraction collector comprising:
  a collection container section configured to set a collection container whose top is open so as to collect a sample flowing out of a detector of a liquid chromatograph; and
  a moving section configured to move in a horizontal plane direction at above the collection container section,
  wherein the moving section comprises:
    a nozzle that is connected to a channel through which a liquid flowing out of the detector flows;
    a nozzle holding section configured to hold the nozzle in such a way that a tip of the nozzle faces downward;
    a waste port, whose top is open, configured to lead a waste liquid to a drain;
    a waste port holding section configured to hold the waste port; and
    a drive mechanism configured to move the nozzle holding section; and
    a waste port drive motor,
  wherein the waste port holding section is formed from an arm, extending in a horizontal direction, configured to hold the waste port at a position lower than the tip of the nozzle,
  wherein the waste port drive motor is configured to move, by rotating the arm, the waste port to the position immediately below the tip of the nozzle and to a position different from the position immediately below the tip of the nozzle, and
  wherein the nozzle tip and the waste port are configured to be moved together by the moving section.

2. The fraction collector according to claim 1, further comprising:
  a collection operation section configured to control the moving section and the waste port drive motor based on a detection signal of the detector so as to perform a collection operation of achieving, when a start point of a peak originating from a sample component is detected, the state where the waste port is not present at the position immediately below the nozzle, before a liquid at a part corresponding to the peak reaches the tip of the nozzle, and of causing the liquid at the part corresponding to the peak to drop from the tip of the nozzle into a collection container for collecting a component corresponding to the peak; and a purge operation section configured to control the waste port drive motor so as to perform, after the collection operation is completed, a purge operation of achieving the state where the waste port is present at the position immediately below the nozzle, and of causing a liquid not containing a sample component to drop from the tip of the nozzle.

3. The fraction collector according to claim 2, wherein the purge operation section is configured to control the drive mechanism so as to perform the purge operation in a state where the moving section is placed at a position at which a next sample component will be dropped into a collection container for collecting the next sample component.

* * * * *